United States Patent [19]

Hoelderich et al.

[11] Patent Number: 4,960,954
[45] Date of Patent: Oct. 2, 1990

[54] PREPARATION OF ENOL ETHERS

[75] Inventors: Wolfgang Hoelderich, Frankenthal; Norbert Goetz, Worms; Leopold Hupfer, Friedelsheim; Walter Himmele, Walldorf, all of Fed. Rep. of Germany

[73] Assignee: BASF Aktiengesellschaft, Ludwigshafen, Fed. Rep. of Germany

[21] Appl. No.: 329,007

[22] Filed: Mar. 27, 1989

[30] Foreign Application Priority Data

Apr. 13, 1988 [DE] Fed. Rep. of Germany ....... 3812236

[51] Int. Cl.$^5$ .............................................. C07C 41/28
[52] U.S. Cl. .................................................. 568/691
[58] Field of Search .......................................... 568/691

[56] References Cited

U.S. PATENT DOCUMENTS

| | | | |
|---|---|---|---|
| 3,021,373 | 2/1962 | Montagna et al. | 568/691 |
| 3,218,359 | 11/1965 | Aguandisch | 568/691 |
| 3,705,924 | 12/1972 | Smith et al. | 568/691 |
| 4,014,941 | 3/1977 | Tanaka et al. | 568/691 |
| 4,409,402 | 10/1983 | Himmele et al. | 568/496 |
| 4,418,216 | 11/1983 | Himmele et al. | 568/497 |
| 4,804,786 | 2/1989 | Fischer et al. | 568/591 |

FOREIGN PATENT DOCUMENTS 0299286 1/1989 European Pat. Off. ............: 568/691

OTHER PUBLICATIONS

Proceedings of the 7th International Zeolite Conference, poster paper 2D-13.

*Primary Examiner*—Werren B. Lone
*Attorney, Agent, or Firm*—John H. Shurtleff

[57] ABSTRACT

Enol ethers of the general formula I

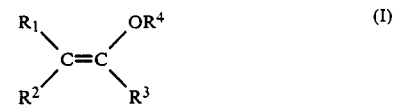

are prepared by eliminating the radical R$^4$OH from acetals or ketals of the formula II

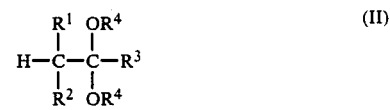

where the substituents
R$^1$ and R$^2$ are each independently of the other hydrogen, C$_1$–C$_{12}$-alkyl, C$_3$–C$_8$cycloalkyl, C$_3$–C$_8$-cycloalkenyl, unsubstituted or C$_1$–C$_4$-alkyl-substituted aryl or C$_7$–C$_{16}$ aralkyl,
R$^3$ is —CR$^5$(OR$^4$)$_2$, —COOR$^4$ or —COR$^4$,
R$^4$ is C$_1$–C$_{20}$-alkyl, C$_7$–C$_{20}$-alkylaryl or C$_7$–C$_{20}$-aralkyl,
R$^5$ is hydrogen or C$_1$–C$_8$-alkyl, in a process which comprises performing the reaction in the presence of phosphoric acid and/or phosphates on a carrier material and/or phosphates and/or zeolites as catalysts.

14 Claims, No Drawings

PREPARATION OF ENOL ETHERS

The present invention relates to a novel and improved process for preparing enol ethers from acetals or ketals containing an α-hydrogen atom.

Enol ethers are in general very useful building blocks in organic synthesis. They are used for preparing specific homopolymers and copolymers, in the fields of paint and adhesive production and as assistants in the textile and leather industry. Furthermore, enol ethers are useful intermediates for organic syntheses, for example for Diels-Alder reactions, for the preparation of glutardialdehydes, γ-pyran and γ-picoline and for the preparation of active substances, such as herbicides, fungicides, insecticides and drugs.

Industrially, enol ethers are prepared by Reppe's method from acetylene and alcohols in the liquid phase with potassium hydroxide as catalyst.

Moreover, enol ethers can be prepared from acetals by alcohol elimination. This reaction can be carried out purely thermally or by homogeneous or heterogeneous catalysis. The catalysts used here are partly limited in versatility, partly in need of improvement as regards activity, selectivity and lifetime.

It is also known that enol ethers may be obtained by eliminating alcohols from acetals over aluminosilicate zeolites (Proceedings of the 7th International Zeolite Conference, poster paper 2D-13). In their acidic H-form, these zeolites show selectivities and conversions which still leave something to be desired. By the additional step of doping the zeolite with Na it is possible to increase the selectivity at incomplete conversion.

The preparation of ethyl vinyl ether over an A-zeolite from acetaldehyde diethyl acetal is known. However, the A-zeolite does not last long at the required reaction temperature of 350° C.; nor can it be freed from the deactivating coke, since at the regenerating temperatures of more than 500° C. required for deactivation the crystal structure of the zeolite is unstable.

It is an object of the present invention to provide a better way of obtaining enol ethers without the disadvantages of existing processes.

We have found that this object is achieved by a novel and improved process for preparing enol ethers by eliminating an alcohol from acetals and ketals, which comprises performing the reaction in the presence of a catalyst selected from the group consisting of (a) phosphoric acid or a hydrogen phosphate on a carrier material, (b) a phosphate and (c) a zeolite.

The enol ethers I are obtainable by the following method:

The reaction takes place by contacting an acetal or ketal containing an α-hydrogen atom with a catalyst in accordance with the following equation:

$$\underset{(II)}{H-\underset{\underset{R^2}{|}}{\overset{\overset{R^1}{|}}{C}}-\underset{\underset{OR^4}{|}}{\overset{\overset{OR^4}{|}}{C}}-R^3} \xrightarrow[-R^4OH]{\Delta} \underset{(I)}{\underset{R^2}{\overset{R^1}{\diagdown}}C=C\underset{R^3}{\overset{OR^4}{\diagup}}}$$

The reaction can be carried out not only in the liquid phase but also in the batchwise or preferably continuous gas phase at from 50° to 500° C. under from 0.01 to 50 bar.

The liquid phase reaction can be carried out for example by the suspension, trickle bed or liquid phase procedure at from 50° to 200° C. under from 0.5 to 20 bar, preferably at from 70° to 170° C. under from 1 to 5 bar. It is advisable to use sparingly volatile or solid acetals or ketals (II) in solution in an inert solvent; per mole of II, from 100 to 500 ml, preferably from 150 to 350 ml, of an inert solvent are in general sufficient.

Suitable inert solvents are ethers, in particular cyclic ethers such as tetrahydrofuran and dioxan, aliphatic hydrocarbons such as n-pentane, the pentane isomer mixture, n-hexane, the hexane isomer mixture, petroleum ethers and cyclohexane, aromatic hydrocarbons such as benzene, toluene, the xylenes and their mixed isomers, or mixtures thereof.

The preferred gas phase reaction can be carried out for example at from 100° to 500° C., preferably at from 150° to 400° C. under from 0.1 to 50 bar, particularly preferably at from 200° to 300° C. under from 0.5 to 5 bar. If the reaction is carried out in the gas phase, the weight hourly space velocity (WHSV) over the catalyst is advantageously from 0.1 to 20, in particular from 0.5 to 8, g of starting material of the formula II per g of catalyst per hour. The gas phase reaction can be carried out in a fixed bed or in a fluidized bed.

After the reaction has ended, the resulting products are isolated from the reaction mixture in a conventional manner, for example by distillation; unconverted starting materials are recycled into the reaction, if appropriate.

In this process, gaseous reaction products are immediately introduced into a separating stage, for example a fractionating column, and split into their individual components. A preferred embodiment comprises quenching the reaction products in aqueous hydrogen carbonate solution, for example $KHCO_3$ or $NaHCO_3/Na_2SO_4$.

The substituents $R^1$ to $R^5$ in the formulae I and II preferably have the following meanings:

$R^1$ and $R^2$ are each independently of the other
hydrogen,
straight-chain or branched $C_1$–$C_{12}$-alkyl, such as methyl, ethyl, n-propyl, isopropyl, n-butyl, isobutyl, sec.-butyl, tert.-butyl, n-pentyl, isopentyl, sec.-pentyl, tert.-pentyl, neopentyl, 1,2-dimethylpropyl, n-hexyl, isohexyl, sec.-hexyl, n-heptyl, isoheptyl, n-octyl, isooctyl, n-nonyl, isononyl, n-decyl, isodecyl, n-undecyl, isoundecyl, n-dodecyl or isododecyl, $C_3$–$C_8$-cycloalkyl, such as cyclopropyl, cyclobutyl, cyclopentyl, cyclohexyl, cycloheptyl or cyclooctyl, aryl, preferably phenyl, 1-naphthyl or 2-naphthyl, particularly preferably phenyl, aryl monosubstituted, disubstituted or trisubstituted by $C_1$–$C_4$-alkyl, such as 2-methylphenyl, 3-methylphenyl, 4-methylphenyl, 2-ethylphenyl, 3-ethylphenyl, 4-ethylphenyl, 2-n-propylphenyl, 3-n-propylphenyl, 4-n-propylphenyl, 3-isopropylphenyl, 4-isopropylphenyl, 2-n-butylphenyl, 3-n-butylphenyl, 4-n-butylphenyl, 3-isobutylphenyl, 4-isobutylphenyl, 3-sec.-butylphenyl, 4-sec.-butylphenyl, 3-tert.-butylphenyl, 4-tert.butylphenyl, 2,4-dimethylphenyl, 2,6-dimethylphenyl, 3,5-dimethylphenyl or 2,4,6-trimethylphenyl, $C_7$–$C_{16}$-aralkyl, preferably $C_7$–$C_{10}$-aralkyl such as benzyl or phenethyl, $C_{7-16}$-aralkyl monosubstituted, disubstituted or trisubstituted by $C_1$–$C_4$-alkyl, preferably $C_1$–$C_4$-alkyl-monosubstituted, -disubstituted or -trisubstituted $C_7$–$C_{10}$-aralkyl such as 4-methylphenyl or 4-methylphenethyl, $R^3$ is—$-CR_5(OR_4)_2$, $-COOR^4$, $-COR^4$, $R^4$ is—straight-chain or branched $C_1$–$C_{20}$-alkyl, preferably straight-chain or branched $C_1$–$C_{12}$-alkyl such as methyl, ethyl, n-propyl, isopropyl, n-butyl, isobutyl, sec.-butyl, tert.-butyl, n-pentyl, isopentyl, sec.-pentyl, tert.-pentyl, neopentyl, 1,2-dimethylpropyl, n-hexyl, isohexyl, sec.-hexyl, n-heptyl, isoheptyl, n-octyl, isooctyl, n-nonyl, isononyl, n-decyl, isodecyl, n-undecyl, isoundecyl, n-dodecyl or isododecyl, $C_7$–$C_{20}$-alkylaryl, preferably $C_7$–$C_{10}$-alkylaryl such as 4-methylphenyl or 4-ethylphenyl, $C_7$–$C_{20}$-aralkyl, preferably $C_7$–$C_{10}$-aralkyl such as benzyl, 1-phenylethyl, 2-phenylethyl, 1-phenyl-n-propyl, 2-phenyl-n-propyl, 2-phenylisopropyl or 3-phenyl-n-propyl, $R_5$ is—hydrogen, $C_1$–$C_8$-alkyl, such as methyl, ethyl, n-propyl, isopropyl, n-butyl, isobutyl, sec.-butyl, tert.butyl, n-pentyl, isopentyl, sec.-pentyl, tert.pentyl, neopentyl, 1,2-dimethylpropyl, n-hexyl, isohexyl, sec.-hexyl, n-heptyl, isoheptyl, n-octyl or isooctyl.

Particularly preferred substituents $R^1$ to $R^5$ in the formulae I and II have the following meanings:

$R^1$ and $R^2$ are each independently of the other hydrogen or $C_1$–$C_4$-alkyl such as methyl, ethyl, n-propyl, isopropyl, n-butyl, isobutyl, sec.-butyl or tert.butyl, $R^3$ is—$CR^5(OR^4)_2$, $-COOR^4$, $-COR^4$, $R^4$ is—$C_1$–$C_2$-alkyl such as methyl or ethyl, and $R^5$ is—hydrogen or $C_1$–$C_2$-alkyl such as methyl or ethyl.

Starting materials of the general formula II are for example 1,1,2,2-tetramethoxypropane, 1,1,2,2-tetraethoxypropane, 1,1,2,2-tetraisobutoxypropane, 1,1,2,2-tetra-n-butoxypropane, 2,2,3,3-tetramethoxybutane, 2,2,3,3-tetra-n-butoxybutane, 2,3,3,3-tetramethoxypentane, 2,2-dimethoxybutane-3-on, 2,2-di-n-butoxybutane-3-on, 3,3-dimethoxyhexane-4-on, methyl 2,2-dimethoxypropionate, isobutyl 2,2,-diisobutoxypropionate, methyl 2,2-dimethoxybutyrate and methyl 2,2-dimethoxy-3-methylbutyrate.

The starting materials are known or preparable in a commonly known manner by acetalation of the corresponding aldehydes.

The catalysts used for the process according to the invention are zeolitic catalysts. Zeolites are crystalline aluminosilicates which possess a highly ordered structure comprising a rigid three-dimensional network of $SiO_4$ and $AlO_4$ tetrahedra joined together by common oxygen atoms. The ratio of the Si and Al atoms: oxygen is 1:2 (see Ullmanns Encyclopadie d. techn. Chemie, 4th edn., vol.24, p.575 (1983)). The electrovalence of the aluminum-containing tetrahedra is balanced by the inclusion in the crystal of cations, for example an alkali metal or hydrogen ion. Cation exchange is possible. The spaces between the tetrahedra are occupied prior to dehydration by drying or calcination by water molecules.

In zeolites, the aluminum in the lattice may also be replaced by other elements such as B, Ga, Fe, Cr, V, As, Sb, Bi or Be or mixtures thereof, or the silicon may be replaced by a tetravalent element such as Ge, Ti, Zr or Hf.

According to structure, zeolites are subdivided into various groups (see Ullmanns Encyclopädie d. techn. Chemie, 4th edn. vol. 24, p. 575 (1983)). For instance, in the mordenite group the zeolite structure is formed by chains and in the chabasite group it is formed by layers of tetrahedra, while in the faujasite group the tetrahedra are arranged into polyhedra, for example in the form of a cuboctahedron composed of 4- or 6-membered rings. Depending on the link into the other of the cuboctahedra, from differently sized voids and pores, zeolites are classified as of Type A, L which arise, X or Y.

Suitable catalysts for the process according to the invention are zeolites of the mordenite group or narrow-pored zeolites of the erionite or chabasite type or zeolites of the faujasite type, for example Y-, X- or L-zeolites. This group of zeolites also includes the ultra-stable zeolites of the faujasite type, i.e. dealuminized zeolites. Processes for preparing such zeolites are described in Catalysis by Zeolites, volume 5 of Studies in Surface Science and Catalysis, ed. B. Imelik et al., Elsevier Scientific Publishing Comp., 1980, page 203, and Crystal Structures of Ultra-stable Faujasites, Advances in Chemistry Series No. 101, American Chemical Society Washington DC, pages 226 et seq. (1971), and in U.S. Pat. No. 4,512,961.

It is particularly advantageous to use zeolites of the pentasil type. Their common building block is a five-membered ring composed of $SiO_4$ tetrahedra. They are characterized by a high $SiO_2/Al_2O_3$ ratio and by pore sizes between those of the zeolites of Type A and those of Type X or Y (of Ullmanns Encyclopädie d. techn. Chemie, 4th edn. vol.24, (1983).

These zeolites may have different chemical compositions. They are aluminosilicate, borosilicate, iron silicate, beryllium silicate, gallium silicate, chromium silicate, arsenic silicate, antimony silicate and bismuth silicate zeolites or mixtures thereof and aluminogermanate, borogermanate, gallium germanate and iron germinate zeolites or mixtures thereof. Specifically, aluminosilicate, borosilicate and iron silicate zeolites of the pentasil type are suitable for the process according to the invention. The aluminosilicate zeolite is prepared for example from an aluminum compound, preferably $Al(OH)_3$ or $Al_2(SO_4)_3$, and from a silicon component, preferably finely divided silicon dioxide, in an aqueous amine solution, in particular in polyamines such as 1,6-hexanediamine or 1,3-propane-diamine or triethylene-tetramine solution, with or in particular without the addition of alkali metal or alkaline earth metal at from 100° to 200° C. under autogenous pressure. This also includes the isotactic zeolites described in EP-A-34,727 and EP-A-46,504. The aluminosilicate zeolites obtained have an $SiO_2/Al_2O_3$ ratio of from 10 to 40,000, depending on the choice of starting quantities. It is also possible to synthesize such aluminosilicate zeolites in an etherial medium, such as diethylene glycol dimethyl ether, in an alcoholic medium such as methanol or 1,4-butanediol, or in water.

The borosilicate zeolite is synthesized for example at from 90° to 200° C. under superatmospheric pressure by reacting a boron compound, for example $H_3BO_3$, with a silicon compound, preferably finely divided silicon dioxide, in an aqueous amine solution, in particular in 1,6-hexanediamine or 1,3-propanediamine or triethyl-enetetramine solution, with or in particular without the addition of an alkali metal or alkaline earth metal. Isotactic zeolites as described in EP-A-34,727 and EP-A-46,504 are also suitable. These borosilicate zeolites can also be prepared by carrying out the reaction not in an aqueous amine solution but in an etherial solution, for example in diethylene glycol dimethyl ether, or in an alcoholic solution, for example 1,6-hexanediol.

The iron silicate zeolite is obtained for example from an iron compound, preferably $Fe_2(SO_4)_3$, and a silicon compound, preferably finely divided silicon dioxide, in an aqueous amine solution, in particular 1,6-hexanediamine, with or without the addition of an alkali metal or alkaline earth metal, at from 100° to 200° C. under autogenous pressure.

The usable high-silicon zeolites ($SiO_2/Al_2O_3 > 10$) also include the ZSM types, ferrierite, Nu-1 and Silicali ® (a molecular sieve, a silica polymorph).

The aluminosilicate, borosilicate and iron silicate zeolites thus prepared, after they have been isolated, dried at from 100° to 160° C., preferably at 110° C., and calcined at from 450° to 550° C., preferably at 500° C., can be molded with a binder in a ratio of from 90:10 to 40:60% by weight into extrudates or tablets. Suitable binders are various aluminum oxides, preferably boehmite, amorphous aluminosilicates having an $SiO_2/Al_2O_3$ ratio of from 25:75 to 90:5, preferably 75:25, silicon dioxide, preferably finely divided $SiO_2$, mixtures of finely divided $SiO_2$ and finely divided $Al_2O_3$, $TiO_2$, $ZrO_2$ and clay. After molding, the extrudates or pellets are dried at 110° C. over 16 h and calcined at 500° C. over 16 h.

Advantageous catalysts are also obtained on molding the isolated aluminosilicate or borosilicate zeolite directly after drying and subjecting it to a calcination only after molding. The synthesized aluminosilicate and borosilicate zeolites can be used in the pure form, without binder, as extrudates or tablets, in which case the extruding or peptizing aids used are for example ethylcellulose, stearic acid, potato starch, formic acid, oxalic acid, acetic acid, nitric acid, ammonia, amines, silicoesters and graphite or mixtures thereof.

If the zeolite, owing to its manner of preparation, is present not in the catalytically active, acidic H-form but for example in the Na-form, it can be completely or partially converted into the desired H-form by ion exchange, for example with ammonium ions, and subsequent calcination or by treatment with acids.

If in the course of the use according to the invention of the zeolitic catalysts deactivation occurs due to the deposition of coke, it is advisable to regenerate the zeolites by burning off the coke deposit with air or with an air/$N_2$ mixture at from 400° to 550° C., preferably at 500° C. This restores the zeolites to their initial activity.

By partial precoking it is possible to set the activity of the catalyst for optimum selectivity in respect of the desired reaction product.

To obtain maximum selectivity, high conversion and long catalyst lives, it is advantageous to modify the zeolites. A suitable modification of the catalyst comprises for example doping the unmolded or molded zeolites with metal salts by ion exchange or impregnation. The metals used are alkali metals such as Li, Cs or K, alkaline earth metals such as Mg, Ca or Sr, metals of main groups 3, 4 and 5 such as Al, Ga, Ge, Sn, Pb or Bi, transition metals of subgroups 4 to 8 such as Ti, Zr, V, Nb, Cr, Mo, W, Mn, Re, Fe, Ru, Os, Co, Rh, Sr, Ni, Pd or Pt, transition metals of subgroups 1 and 2 such as Cu, Ag or Zn, or rare earth metals such as La, Ce, Pr, Nd, Fr, Yb or U.

Advantageously, the doping is carried out by introducing the molded zeolites initially in a riser tube and passing an aqueous or ammoniacal solution of a halide or a nitrate of a metal as described over it at from 20° to 100° C. Such an ion exchange can be effected for example, on the hydrogen, ammonium and alkali metal form of the zeolite. A further way of applying metal to the zeolite comprises impregnating the zeolitic material, for example with a halide, a nitrate or an oxide of the metals described in aqueous, alcoholic or ammoniacal solution. Not only ion exchange but also impregnation are followed by at least one drying operation, alternatively by a further calcination.

A possible embodiment comprises dissolving $Cu(NO_3)_2 \times 3H_2O$ or $Ni(NO_3)_2 \times 6H_2O$ or $Ce(NO_3)_3 \times 6H_2O$ or $La(NO_3)_2 \times 6H_2O$ or $Cs_2CO_3$ in water. The molded or unmolded zeolite is impregnated with this solution for a certain time, say 30 minutes. Any supernatant solution is stripped of water in a rotary evaporator. Thereafter the impregnated zeolite is dried at about 150° C. and calcined at about 550° C. This impregnation can be carried out repeatedly in succession in order to obtain the desired metal content.

It is also possible to prepare, for example an aqueous $Ni(CO_3)_2$ solution or ammoniacal $Pd(NO_3)_2$ solution and to suspend the pure pulverulent zeolites therein at from 40° to 100° C. by stirring for about 24 hours. Following filtration, drying at about 150° C. and calcination at about 500° C., the zeolitic material thus isolated can be further processed with or without binders into extrudates, pellets or fluidizable material.

An ion exchange on the zeolites present in the H-form or ammonium form or alkali metal form can be effected by introducing the zeolites initially in extrudates or pellets into a column and passing, for example, an aqueous $Ni(NO_3)_2$ solution or ammoniacal $Pd(NO_3)_2$ solution at a slightly elevated temperature of from 30° to 80° C. over it in a cycle for from 15 to 20 hours. This is followed by washing with water, drying at about 150° C. and calcining at about 550° C. With some metal-doped zeolites such as the Pd-, Cu- or Ni-doped zeolites, an aftertreatment with hydrogen is advantageous.

A further modifying technique comprises subjecting the zeolitic material, molded or unmolded, to a treatment with acids such as hydrochloric acid, hydrofluoric acid and phosphoric acid and/or steam. An advantageous procedure is to treat zeolites in powder form with 1N phosphoric acid at 80° C. for 1 hour, washing with water, drying at 110° C. over 16 h and calcining at 500° C. over 20 h. In another procedure, zeolites are treated before or after molding with binders with from 3 to 25% strength by weight, in particular from 12 to 20% strength by weight, aqueous hydrochloric acid at from 60° to 80° C., for example from 1 to 3 hours. Thereafter the zeolite thus treated is washed with water, dried and calcined at from 400° to 500° C.

A particular form of the acid treatment comprises treating the zeolitic material before it is molded with in general from 0.001N to 2N, preferably from 0.05N to 0.5N, hydrofluoric acid for from in general 0.5 to 5, preferably from 1 to 3, hours at an elevated temperature, for example by refluxing. After the zeolitic material is isolated for example by filtration and washed, it is advantageously dried, for example at from 100° to 160° C., and calcined at in general from 450° to 600° C. In another preferred form of the acid treatment, the zeolitic material, after molding with binder, is treated at elevated temperatures, advantageously at from 50° to 90° C., preferably at from 60° to 80° C., preferably with from 12 to 20% strength by weight hydrochloric acid for from 0.5 to 5 hours. Thereafter the zeolitic material is in general washed and advantageously dried, for example at from 100° to 160° C., and calcined at in general from 450° to 600° C. An HF treatment may also be followed by an HCl treatment.

In another procedure, zeolites can be modified by applying phosphorus compounds, such as trimethoxyphosphate, trimethoxyphosphine or primary, secondary or tertiary sodium phosphate. The treatment with primary sodium phosphate has proved particularly advantageous. Here the zeolites are impregnated in extruded, tablet or fluidized form with aqueous $NaH_2PO_4$ solution, dried at 110° C. and calcined at 500° C.

Further catalysts for the preparation of the bifunctional building blocks according to the invention are phosphates, in particular aluminum phosphates, silicon aluminum phosphates, silicon iron aluminum phosphates, cerium phosphates, zirconium phosphates, boron phosphates, iron phosphates, strontium phosphates and mixtures thereof.

Aluminum phosphate catalysts used for the process according to the invention are in particular hydrothermally synthesized aluminum phosphates.

Hydrothermally synthesized aluminum phosphates are for example APO-5, APO-9, APO-11, APO-12, APO-14, APO-21, APO-25, APO-31 and APO-33. Syntheses of these compounds are described in EP No. 132,708, U.S. Pat. Nos. 4,310,40 and 4,473,663.

$AlPO_4$-5 (APO-5) for example is synthesized by homogeneously mixing orthophosphoric acid with pseudoboehmite (Catapal SB ®) in water, adding tetrapropylammonium hydroxide, and then reacting in an autoclave at about 150° C. under autogenous pressure for from 20 to 60 hours. The $AlPO_4$ is filtered off, dried at from 100° to 160° C. and calcined at from 450° to 550° C.

$AlPO_4$-9 (APO-9) is synthethized from orthophosphoric acid and pseudoboehmite in aqueous DABCO solution (1,4-diazabicyclo[2.2.2]octane) at about 200° C. under autogenous pressure in the course of from 200 to 400 hours.

$AlPO_4$-21 (APO-21) is synthesized from orthophosphoric acid and pseudoboehmite in aqueous pyrrolidone solution at from 150° to 200° C. under autogenous pressure in the course of from 50 to 200 hours.

The silicon aluminum phosphates used for the process according to the invention are for example SAPO-5, SAPO-11, SAPO-31 and SAPO-34. The synthesis of these compounds is described, for example, in EP No. 103,117 and U.S. Pat. No. 4,440,871. SAPOs are prepared by crystallization from aqueous mixture at from 100 to 250° C. under autogenous pressure in the course of from 2 hours to 2 weeks, during which the reaction mixture comprising a silicon component, an aluminum component and a phosphorus component is converted in aqueous organoamine solutions.

SAPO-5, for example, is obtained by mixing $SiO_2$ suspended in aqueous tetrapropylammonium hydroxide solution with an aqueous suspension of pseudoboehmite and orthophosphoric acid and subsequent reaction at 150°–200°C. for from 20 to 200 hours under autogenous pressure in a stirred auto-clave. The powder is filtered off, dried at from 110° to 160° C. and calcined at from 450° to 550° C.

Phosphorus catalysts used for the process also include precipitated aluminum phosphates. Such aluminum phosphate is prepared for example by dissolving 92 g of diammonium hydrogenphosphate in 700 ml of water. 260 g of $Al(NO_3)_3 \times H_2O$ in 700 ml of water are added dropwise over 2 hours, during which the pH is maintained at pH 8 by the simultaneous addition of 25% strength $NH_3$ solution. The resulting precipitate is subsequently stirred for 12 hours, and then filtered off with suction and washed. It is dried at 60° C. over 16 h.

Boron phosphates for the process according to the invention can be prepared for example by mixing and kneading concentrated boric acid and phosphoric acid and subsequent drying and calcination in an inert gas, air or steam atmosphere at from 250° to 650° C., preferably at from 300° to 550° C.

Cerium phosphate for the process according to the invention is obtained for example by precipitation from 52 g of $Ce(NO_3)_3 \times 6H_2O$ and 56 g of $NaH_2PO_4 \times 2H_2O$. After filtration, the material is molded into extrudates, dried at 120° C. and calcined at 450° C.

Phosphoric acid is applied to $SiO_2$, $Al_2O_3$ or pumice carrier material, for example by impregnating or spraying. A catalyst which contains phosphoric acid can be obtained for example by impregnating $SiO_2$ with $H_3PO_4$, $NaH_2PO_4$ or $Na_2HPO_4$ solution and subsequent drying or calcination. However, phosphoric acid can also be sprayed together with silica gel in a spray tower; this is followed by a drying step and usually by a calcination. Phosphoric acid can also be sprayed onto the carrier material in an impregnating mill.

The catalysts described here can be optionally used as from 2 to 4 mm extrudates or as tablets from 3 to 5 mm in diameter or as chips from 0.1 to 0.5 mm in particle size or in fluidizable form.

The enol ethers I can be used for the preparation of aldehydes in a conventional manner by reaction with carbon monoxide and hydrogen. For this use of the compounds I, preference is given to those compounds which do not contain any unsaturated non-aromatic carbon-carbon bonds in $R^1$ to $R^5$.

They can be hydroformylated in a conventional manner in accordance with the following equation:

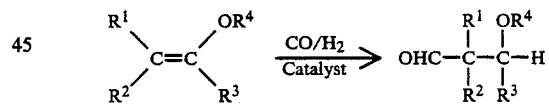

Suitable catalysts are for example Rh-containing catalysts.

The following Examples illustrate the invention:
Preparation of the catalysts

Catalyst A

The borosilicate zeolite of the pentasil type is prepared in a hydrothermal synthesis from 640 g of finely divided $SiO_2$, 122 g of $H_3BO_3$ and 8000 g of an aqueous 1,6-hexadiamine solution (mixture 50:50% by weight) at 170° C. under autogenous pressure in a stirred auto-clave. After filtration and washing, the crystalline reaction product is dried at 100° C. over 24 h and calcined at 500° C. over 24 h. This borosilicate zeolite is composed of 94.2% by weight of $SiO_2$ and 2.3% by weight of $B_2O_3$.

This material is used to produce by molding with a molding aid 2 mm extrudates which are dried at 100° C. over 16 h and calcined at 500° C. over 24 h.

Catalyst B

An aluminosilicate zeolite of the pentasil type is prepared under hydrothermal conditions under autogenous pressure and at 150° C. from 65 g of finely divided $SiO_2$ and 20.3 g of $Al_2(SO_4)_3 \times 18H_2O$ in 1 kg of an aqueous 1,6-hexanediamine solution (mixture 50:50% by weight) in a stirred autoclave. The crystalline reaction product is filtered off, washed, dried at 110° C. over 24 h and calcined at 500° C. over 24 h. This aluminosilicate zeolite contains 91.6% by weight of $SiO_2$ and 4.6% by weight of $Al_2O_3$. The catalyst is molded with a molding aid into 2 mm extrudates, dried at 110° C. over 16 h and calcined at 500° C. over 24 h.

Catalyst C

Catalyst C is obtained by impregnating the extrudates of Catalyst A with an aqueous $Cs_2CO_3$ solution, then drying at 130° C. over 2 h and calcining at 540° C. over 2 h. The Cs content is 0.6% by weight.

Catalyst D 200 g of the borosilicate zeolite described under catalyst A are ion exchanged at room temperature with 1 l of an aqueous solution of 16.7 g of $FeCl_3 \times 6H_2O$ and 50 g of $NH_4Cl$ over 24 h, then thoroughly washed Cl-free with $H_2O$, dried at 150° C. over 1 h and calcined at 500° C. over 2 h. This powder is molded with finely divided $SiO_2$ in a weight ratio of 70:30. After drying, the extrudates are calcined at 500° C. over 16 h.

Catalyst E

Catalyst E is prepared in the same way as catalyst C, except that $Cs_2CO_3$ is replaced by $Ce(NO_3)_2$. The Ce content is 1.65% by weight.

Catalyst F $AlPO_4$-12 (APO-12) is synthetized by dissolving and suspending 200 g of 98% strength phosphoric acid 136 g of boehmite respectively in 400 g of water, adding an aqueous solution of 60 g of ethylenediamine and 320 g of $H_2O$, and reacting this mixture in a stirred autoclave at 200° C. under autogenous pressure for 24 hours. The crystalline material is filtered off, dried at 120° C. and calcined at 500° C. over 16 h. The $AlPO_4$-12 thus synthesized contains 55.5% by weight of $P_2O_5$ and 39.7 by weight of $Al_2O_3$. This material is molded with extrusion aids into 3 mm extrudates, dried once more at 120° C. and calcined at 500° C. over 6 h.

Catalyst G

Silicon aluminum phosphate-5 (SAPO-5) is prepared from a mixture of 200 g of 98% strength phosphoric acid, 136 g of boehmite, 60 g of silica sol (30% strength), 287 g of tripropylamine and 587 g of $H_2O$. This mixture is reacted at 150° C. under autogenous pressure for 168 hours. The crystalline product is filtered off, dried at 120° C. and calcined at 500° C. SAPO-5 contains 49.8% by weight of $P_2O_5$, 33.0% by weight of $Al_2O_3$ and 6.2% by weight of $SiO_2$. SAPO-5 is molded with an extrusion aid into 3 mm extrudates, dried at 120° C. and calcined at 500° C.

Catalyst H

Commercial zirconium phosphate $Zr_3(PO_4)_4$ is molded.

Catalyst I $CePO_4$ is obtained by precipitation from 52 g of $Ce(NO_3)_3 \times 6H_2O$ and 56 g of $NaH_2PO_4 2H_2O$. After filtration, the material is molded into extrudates, dried at 120° C. and calcined at 450° C. Catalyst I contains 47.1% by weight of Ce and 12.7% by weight of P.

EXAMPLES

EXAMPLES 1 to 9

The enol ethers were prepared by the following method:

The reactions were carried out in the gas phase under isothermal conditions in a tubular reactor (coil, 0.6 cm internal diameter, 90 cm length) over no less than 6 hours. The reaction products were separated off and characterized in a conventional manner. It is advisable to quench the reaction gas with methanol and to neutralize the solution with aqueous sodium bicarbonate in order to prevent dimerization or back reaction. The quantitative determination of the reaction products and of the starting materials was done by gas chromatography. The GC analyses were carried out after 6 hours.

TABLE

|  | 1,1,2,2-etramethoxypropane | | | 1,1,2-trimethoxyprop-2-ene + methanol | | | | | |
|---|---|---|---|---|---|---|---|---|---|
| Example | 1 | 2 | 3 | 4 | 5 | 6 | 7 | 8 | 9 |
| Catalyst | A | B | C | D | E | F | G | H | I |
| Temperature °C. | 250 | 250 | 250 | 250 | 250 | 250 | 250 | 250 | 250 |
| WHSV $h^{-1}$ | 2 | 2 | 2 | 2 | 2 | 2 | 2 | 2 | 2 |
| Conversion % (II) | 100 | 100 | 100 | 100 | 100 | 100 | 100 | 100 | 100 |
| Selectivity % (II) | 94.7 | 89.5 | 92.3 | 96.3 | 95.1 | 85.2 | 91.8 | 89.5 | 93.1 |

Preparation of 1,1,2-trimethoxyprop-2-ene

EXAMPLE 10

60 ml/h of 1,1,2,2-tetramethoxypropane (dissolved in THF 50:50% by weight) are vaporized in a nitrogen stream of 200 l/h and passed at 260° C. over 1 l of a boron zeolite catalyst (catalyst A) contained in a reaction tube electrically heated from the outside.

The gaseous reaction mixture is condensed over a 10-hour period and collected in a cold trap at −80° C. The 1,1,2-trimethoxyprop-2-ene (2-methoxyacrolein dimethyl acetal) is purified in a simple manner by conventional distillation.

The conversion is 98.9% and the selectivity 89.4%.

EXAMPLE 11

The procedure of Examples 1 to 9 is followed, except that the temperature is 270° C. and the total duration is 74 hours.

The gaseous reaction mixture is introduced into the middle portion of a fractionating column, and the methanol formed and other low boilers are distilled off overhead, while 1,1,2-trimethoxyprop-2-ene together with small amounts of unconverted starting material can be withdrawn at the base of the column.

The powder is purified in a simple manner by conventional distillation.

The conversion of 1,1,2,2-tetramethoxypropane is >98% and the distillation yield 87.2%.

EXAMPLE 12

In the same apparatus and over the same catalyst as in Example 1, 120 ml/h 1,1,2,2-tetramethoxypropane are vaporized in a nitrogen stream of 200 l/h and reacted at 230° C. The reaction was carried out for 20 hours.

The gaseous reaction mixture was quenched with methanol and introduced into a saturated aqueous sodium carbonate solution.

Conventional working-up shows 100% conversion and a selectivity of 70.5% in respect of 1,1,2-trimethoxyprop-2-ene.

The following Examples describe the use of the enol ethers:

Preparation of 3,4,4,-triisobutoxybutanal

EXAMPLE 13

In a miniautoclave (reaction space 300 ml) equipped with a magnetic stirrer, 71 g of 2,3,3-triisobutoxyprop-1-ene are dissolved in 70 g of tetrahydrofuran. 150 mg of Rh$_2$(COD)$_2$Cl$_2$ (COD=cycloocta-1,5-diene) are added as oxo reaction catalyst. The hydroformylation is carried out at 110° C. under a synthesis gas pressure (CO:H$_2$=1:1) of 300 bar. Subsequently 300 bar of synthesis gas are injected in the course of 20 hours. The reaction mixture of 147 g is worked-up by fractional distillation. 80 g pass over within the range 118°-136° C. under 2 mbar. According to NMR, 13CNMR and IR analysis, 3,4,4-triisobutoxybutanal has been obtained.

EXAMPLE 14

A 10 1 magnetic lift stirred autoclave is charged with 1,015 g of 2,3,3-trimethoxyprop-1-ene together with 3,000 g of tetrahydrofuran and 500 mg of Rh$_2$(COD)$_2$Cl$_2$ as hydroformylation catalyst. The oxo reaction is carried out under a pressure of 500 bar (CO/H$_2$=1:1) at 40° C. for 6 hours, at 60° C./550 bar for another 6 hours and at 80° C./600 bar for a further 6 hours. According to gas chromatography, this way of carrying out the reaction gives a conversion of 94%. The desired compound 3,4,4-trimethoxybutanal (bp=135° C./110 mbar) is obtained in the yield of 87% following fraction-ation. Preparation of methyl 2-methoxyacrylate

EXAMPLE 15

100 ml/h of methyl 2,2-dimethoxypropionate are vaporized in a nitrogen stream of 300 l/h and passed at 230° C. over 1 l of catalyst A housed inside a reaction tube electrically heated from the outside. The gaseous reaction mixture is condensed over a 10-hour period and quenched in a buffer solution of pH 7.

Conventional working-up shows the conversion to be 100% and the selectivity for methyl 2-methoxyacrylate 94.5%.

We claim:

1. A process for preparing an enol ether of the formula

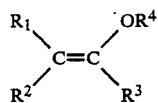

by eliminating the radical R$^4$OH from an acetal or ketal of the formula

where
R$^1$ and R$^2$ are each independently of the other hydrogen, C$_1$-C$_{12}$-alkyl, C$_3$-C$_8$-cycloalkyl, C$_3$-C$_8$-cycloalkenyl, unsubstituted or C$_1$-C$_4$-alkyl-substituted aryl or C$_7$-C$_{16}$-aralkyl;
R$^3$ is —CR$^5$(OR$^4$)$_2$, —COOR$^4$ or —COR$^4$;
R$^4$ is C$_1$-C$_{20}$-alkyl, C$_7$-C$_{20}$-alkylaryl or C$_7$-C$_{20}$-aralkyl and;
R$^5$ is hydrogen or C$_1$-C$_8$-alkyl,
wherein comprises performing the reaction at from 50° to 500° C., under a pressure of from 0.1 to 50 bar and in the presence of a catalyst selected from the group consisting of (a) phosphoric acid or a hydrogen phosphate on a carrier material, (b) a phosphate, and (c) a zeolite.

2. A process as claimed in claim 1, wherein the reaction is carried out at from 50° to 500° C.

3. A process as claimed in claim 1, wherein the reaction is carried out under from 0.1 to 50 bar.

4. A process as claimed in claim 1, wherein the reaction is carried out in the gas phase with or without an inert carrier gas at from 150° to 400° C. under from 0.5 to 5 bar.

5. A process as claimed in claim 1, wherein the reaction is carried out in the liquid phase in the presence or absence of an inert solvent at from 50° to 200° C. under from 0.5 to 20 bar.

6. A process as claimed in claim 1, wherein the substituents
R$^1$ and R$^2$ are each independently of the other hydrogen or C$_1$-C$_4$-alkyl,
R$^3$ is —CR$^5$(OR$^4$)$_2$, —COOR$^4$ or —COR$^4$,
R$^4$ is methyl or ethyl,
R$^5$ is hydrogen, methyl or ethyl.

7. A process as claimed in claim 1,
wherein the reaction is carried out in the presence of a mono- or dihydrogenphosphate of sodium on a carrier material or a boron, aluminum, zirconium, iron or strontium phosphate or a mixture thereof.

8. A process as claimed in claim 1, wherein the reaction is carried out in the presence of a borosilicate, aluminosilicate or iron silicate zeolite or a zeolite doped with an alkali metal, a transition metal or a rare earth metal, or a zeolite of the pentasil or faujasite type or a mixture thereof.

9. A process as claimed in claim 1, wherein the catalyst is a pentasil zeolite.

10. A process as claimed in claim 9, wherein the catalyst is a borosilicate zeolite of the pentasil type.

11. A process as claimed in claim 9, wherein the catalyst is an aluminosilicate zeolite of the pentasil type.

12. A process as claimed in claim 1, wherein the catalyst is an aluminum phosphate.

13. A process as claimed in claim 1, wherein the catalyst is a silicon aluminum phosphate.

14. A process as claimed in claim 1 wherein the catalyst is a phosphate of an element selected from the group consisting of aluminum, iron, cerium, zirconium, boron and mixtures thereof.

* * * * *

UNITED STATES PATENT AND TRADEMARK OFFICE
CERTIFICATE OF CORRECTION

PATENT NO. : 4,960,954

DATED : October 2, 1990

INVENTOR(S) : Wolfgang Hoelderich, Norbert Goetz, Leopold Hupfer and Walter Himmele It is certified that error appears in the above-identified patent and that said Letters Patent is hereby corrected as shown below:

ON THE TITLE PAGE,
IN THE ABSTRACT:

Line 10 from the bottom: change "$C_3$-$C_8$cycloalkyl" to

-- $C_3$-$C_8$-cycloalkyl --.

IN THE CLAIMS:

Claim 1, Col. 12, line 18: change "wherein" to -- which --.

Claim 1, Col. 12, line 39: change "-$CR^5(OR^4)^2$" to

-- -$CR^5(OR^4)_2$ --.

Signed and Sealed this

Seventh Day of January, 1992

Attest:

HARRY F. MANBECK, JR.

*Attesting Officer*   *Commissioner of Patents and Trademarks*